US011197617B2

(12) United States Patent
Berkow et al.

(10) Patent No.: US 11,197,617 B2
(45) Date of Patent: Dec. 14, 2021

(54) SYSTEMS AND METHODS FOR MONITORING AND ANALYZING CARDIOVASCULAR STATES

(71) Applicant: Intelomed, Inc., Wexford, PA (US)

(72) Inventors: Jan Berkow, Wexford, PA (US); Anne Brumfield, Cranberry Township, PA (US)

(73) Assignee: Intelomed, Inc., Cranberry Township, PA (US)

(*) Notice: Subject to any disclaimer, the term of this patent is extended or adjusted under 35 U.S.C. 154(b) by 721 days.

(21) Appl. No.: 15/804,440

(22) Filed: Nov. 6, 2017

(65) Prior Publication Data

US 2018/0055377 A1    Mar. 1, 2018

Related U.S. Application Data

(63) Continuation of application No. 14/457,946, filed on Aug. 12, 2014, now Pat. No. 9,808,160.

(Continued)

(51) Int. Cl.
*A61B 5/0205* (2006.01)
*A61B 3/16* (2006.01)
(Continued)

(52) U.S. Cl.
CPC ........... *A61B 5/0205* (2013.01); *A61B 3/16* (2013.01); *A61B 5/02108* (2013.01);
(Continued)

(58) Field of Classification Search
CPC ..... A61B 5/0205; A61B 5/746; A61B 5/7275; A61B 5/7257; A61B 3/16; A61B 5/02108;
(Continued)

(56) References Cited

U.S. PATENT DOCUMENTS 4,450,527 A   5/1984  Sramek
5,206,807 A   4/1993  Hatke et al.
(Continued)

FOREIGN PATENT DOCUMENTS

EP   1601287 A1   12/2005
EP   2392257 A2   12/2011
(Continued)

OTHER PUBLICATIONS

European Patent Office; Search Report in related European Patent Application No. 14835979.7 dated Mar. 7, 2017.
(Continued)

*Primary Examiner* — Sanjay Cattungal
(74) *Attorney, Agent, or Firm* — Wood Herron & Evans LLP

(57) ABSTRACT

A system and method for hemodynamic dysfunction detection may include at least one sensor configured to received one or more signals from a patient, a computing device in data communication with the at least one sensor, a computer-readable storage medium in communication with the computing device, an input device, and an output device. The system may include computer readable instructions to cause the system to receive at least one signal in the time domain from the sensor, determine at least one metric in the frequency domain from the at least one signal in the time domain, and determine the cardiovascular state of the patient from a combination of the at least one metric in the frequency domain and information contained in at least one database of cardiovascular states. The system may also notify a user of a immanent patient cardiovascular event and recommend one or more interventions to mitigate it.

37 Claims, 9 Drawing Sheets

Related U.S. Application Data

(60) Provisional application No. 61/865,114, filed on Aug. 12, 2013.

(51) Int. Cl.

| | | |
|---|---|---|
| *A61B 5/021* | (2006.01) | |
| *A61B 5/024* | (2006.01) | |
| *A61B 5/00* | (2006.01) | |
| *G16H 50/20* | (2018.01) | |
| *G16H 40/67* | (2018.01) | |
| *G16H 40/63* | (2018.01) | |
| *G16H 20/30* | (2018.01) | |
| *G16H 20/40* | (2018.01) | |
| *A61B 5/053* | (2021.01) | |
| *A61B 5/08* | (2006.01) | |
| *A61B 5/16* | (2006.01) | |
| *A61B 5/349* | (2021.01) | |

(52) U.S. Cl.
CPC ........ *A61B 5/02416* (2013.01); *A61B 5/7257* (2013.01); *A61B 5/7275* (2013.01); *A61B 5/746* (2013.01); *G16H 20/30* (2018.01); *G16H 20/40* (2018.01); *G16H 40/63* (2018.01); *G16H 40/67* (2018.01); *G16H 50/20* (2018.01); *A61B 5/002* (2013.01); *A61B 5/0022* (2013.01); *A61B 5/053* (2013.01); *A61B 5/08* (2013.01); *A61B 5/165* (2013.01); *A61B 5/349* (2021.01); *A61B 5/4848* (2013.01); *A61B 5/7278* (2013.01); *A61B 5/7282* (2013.01); *A61B 5/7405* (2013.01); *A61B 5/7475* (2013.01)

(58) Field of Classification Search
CPC . A61B 5/02416; A61B 5/7278; A61B 5/0452; A61B 5/08; A61B 5/165; A61B 5/4848; A61B 5/0022; A61B 5/002; A61B 5/7405; A61B 5/7282; A61B 5/7475; A61B 5/053; G16H 20/30; G16H 20/40; G16H 50/20; G16H 40/67; G16H 40/63
See application file for complete search history.

(56) References Cited

U.S. PATENT DOCUMENTS

| | | |
|---|---|---|
| 5,292,339 A | 3/1994 | Stephens et al. |
| 5,370,122 A | 12/1994 | Kunig et al. |
| 5,810,011 A | 9/1998 | Kunig |
| 5,830,131 A | 11/1998 | Caro et al. |
| 5,860,918 A | 1/1999 | Schradi et al. |
| 5,865,756 A | 2/1999 | Peel, III |
| 5,900,433 A | 5/1999 | Igo et al. |
| 6,112,115 A | 8/2000 | Feldman et al. |
| 6,126,595 A | 10/2000 | Amano et al. |
| 6,217,522 B1 | 4/2001 | Shoshan |
| 6,270,461 B1 | 8/2001 | Chio |
| 6,287,608 B1 | 9/2001 | Levin et al. |
| 6,315,735 B1 | 11/2001 | Joeken et al. |
| 6,334,849 B1 | 1/2002 | Sunagawa |
| 6,339,716 B1 | 1/2002 | Sawada et al. |
| 6,371,922 B1 | 4/2002 | Baumann et al. |
| 6,485,431 B1 | 11/2002 | Campbell |
| 6,575,912 B1 | 6/2003 | Turcott |
| 6,719,705 B2 | 4/2004 | Mills |
| 6,776,764 B2 | 8/2004 | Pinsky |
| 6,858,006 B2 | 2/2005 | MacCarter et al. |
| 7,044,918 B2 | 5/2006 | Diab |
| 7,285,090 B2 | 10/2007 | Stivoric et al. |
| 7,324,848 B1 | 1/2008 | Turcott |
| 7,328,053 B1 | 2/2008 | Diab et al. |
| 7,330,750 B2 | 2/2008 | Erkkila et al. |
| 7,678,057 B2 | 3/2010 | Berkow et al. |
| 7,794,406 B2 | 9/2010 | Reisfeld et al. |
| 7,848,810 B1 * | 12/2010 | Nabutovsky ....... A61N 1/36542 607/17 |
| 8,423,108 B2 | 4/2013 | Berkow |
| 9,002,440 B2 | 4/2015 | Berkow et al. |
| 9,808,160 B2 | 11/2017 | Berkow et al. |
| 10,772,512 B2 * | 9/2020 | Klaassen ................ A61B 5/681 |
| 2001/0049476 A1 | 12/2001 | Forstner |
| 2002/0045806 A1 | 4/2002 | Baker et al. |
| 2003/0167010 A1 | 9/2003 | Pinsky |
| 2004/0039273 A1 | 2/2004 | Terry |
| 2005/0197675 A1 | 9/2005 | David et al. |
| 2006/0167515 A1 | 7/2006 | Stickney et al. |
| 2006/0293384 A1 | 12/2006 | Whewell |
| 2007/0032732 A1 | 2/2007 | Shelley et al. |
| 2007/0088222 A1 | 4/2007 | Berkow et al. |
| 2007/0123787 A1 | 5/2007 | Kitajima et al. |
| 2007/0255146 A1 | 11/2007 | Andrews et al. |
| 2008/0045844 A1 | 2/2008 | Arbel |
| 2008/0167564 A1 | 7/2008 | Hete et al. |
| 2008/0228090 A1 | 9/2008 | Wariar et al. |
| 2008/0230705 A1 * | 9/2008 | Rousso ................... A61B 5/417 250/363.04 |
| 2008/0255471 A1 | 10/2008 | Naghavi et al. |
| 2008/0269625 A1 | 10/2008 | Halperin et al. |
| 2009/0076399 A1 | 3/2009 | Arbel |
| 2010/0081947 A1 | 4/2010 | Suzuki |
| 2010/0249543 A1 * | 9/2010 | Sethi ..................... A61B 5/4824 600/301 |
| 2010/0249555 A1 * | 9/2010 | Sethi ..................... A61B 5/726 600/324 |
| 2010/0249556 A1 * | 9/2010 | Sethi ..................... A61B 5/726 600/324 |
| 2011/0046498 A1 * | 2/2011 | Klap .................... A61B 5/7275 600/534 |
| 2011/0112442 A1 * | 5/2011 | Meger .................. A61B 5/4094 600/595 |
| 2011/0245691 A1 | 10/2011 | Silber |
| 2012/0029373 A1 | 2/2012 | Stadler et al. |
| 2012/0029374 A1 * | 2/2012 | Berkow ............. A61B 5/02116 600/526 |
| 2013/0080489 A1 | 3/2013 | Ochs et al. |
| 2013/0267858 A1 * | 10/2013 | Berkow ............... A61B 5/7278 600/479 |
| 2014/0151563 A1 * | 6/2014 | Rousso .................. G01T 1/161 250/362 |

FOREIGN PATENT DOCUMENTS

| | | |
|---|---|---|
| EP | 2540222 A2 | 1/2013 |
| WO | 03077854 A2 | 9/2003 |
| WO | 2004084720 A2 | 10/2004 |
| WO | 2005107584 A1 | 11/2005 |
| WO | 2014143962 A2 | 9/2014 |

OTHER PUBLICATIONS

Tao et al.; An Ultrawideband Radar Based Pulse Sensor for Arterial Stiffness Measurement (2007).

Cruz et al.; Algorithm Fusion for the Early Detection of Apnea-Bradycardia in Preterm Infants, Computers in Cardiology, (Sep. 17, 2006); 473-476 <http://ieeexplore.ieee.org/xpl/login.jsp?arnumber=4511891>.

Feiseel et al.; Respiratory Variation of Plethysmography Signal with a Pulse Oximeter: New Predictive Parameters of Fluid Responsiveness?, Proceedings of the American Thoracic Society, (Apr. 2006); 3:A295.

Kim et al.; Can Cardiac Contractility be Estimated by an Inspiratory Hold Manueuver?, Proceedings of the American Thoracic Society, (Apr. 2006); 3:A296.

Kim et al.; Determinates of Arterial Pulse Pressure and Stroke Volume Variation during Positive-Pressure Ventilation, Proceedings of the American Thoracic Society, (Apr. 2006); 3:A297.

Lamia et al.; Brachial Pulse Pressure is Related to Total Arterial Compliance and Stroke Volume in ICU Patients: An Arterial Tonometric Study, Proceedings of the American Thoracic Society, (Apr. 2006); 3:A296.

(56) References Cited

OTHER PUBLICATIONS

Monnet et al.; Measuring Aortic Diameter is Essential for Assessing Fluid Challenge by Esphageal Doppler, Proceedings of the American Thoracic Society, (Apr. 2006); 3:A296.
Pravisani et al.; Short Term Prediction of Severe Bradycardia in Premature Newborns, Computers in Cardiology, (Sep. 21, 2003); 725-728.
Portet et al.; Evaluation of On-Line Bradycardia Boundary Detectors from Neonatal Clinical Data, Conf IEEE Engl Med Biol Soc.; (Aug. 22, 2007); 3288-3291.
Ridel et al.; Prediction of Fluid Responsiveness in Spontaneously Breathing Patients: Response to Passive Leg Raising Measured by Pulse Contour Cardiac Output, Proceedings of the American Thoracic Society; (Apr. 2006); 3:A295.
Zamanian et al.; Assessment of Cardiac Function and Ventilatory Efficiency by Noninvasive CO2 Monitoring during Reduction of Ventilatory Support in Patients with CHF; Proceedings of the American Thoracic Society; (Apr. 2006); 3:A296.
European Patent Office; Search Report in related International Patent Application No. PCT/US2014/040890 dated Nov. 4, 2014.

* cited by examiner

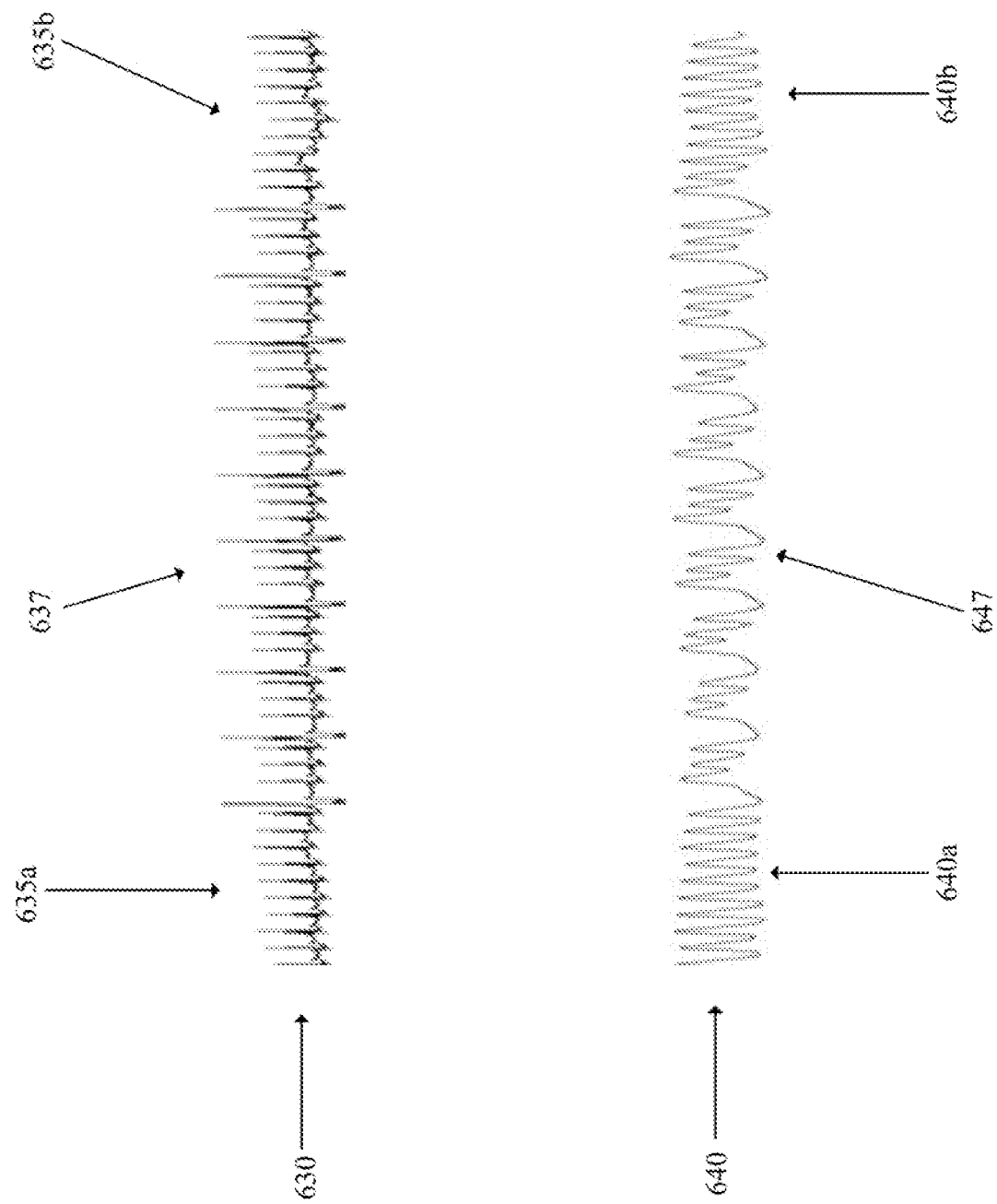

| Derived Parameters | % Δ Pulse Amplitude (Tissue Perfusion) | % Δ Pulse Rate (Autonomic Stress) | Frequency of Dysrhythmias (Myocardial Ischemia) | Repiration to Cardiac Frequency Strength Ratio (Respiratory Distress) | Pulse Volume Alteration (Vascular Compliance) | SpO2 (Pulse Oximetry) |
|---|---|---|---|---|---|---|
| Stress Related Events | | | | | | |
| Obstructive Sleep Disorder Event Detection | → | → | ← | X | → | → |
| Anesthesia induced Hypovolemia | → | ← | ← | ← | → | → |
| Typical Hemodialysis Induced Hypovolemia | → | ← | ← | X | ← | → |
| Hemodialysis Induced Hypovolemia on Heart Failure Patient | →→ | ←← | ← | ← | → | → |

FIG. 7

SYSTEMS AND METHODS FOR MONITORING AND ANALYZING CARDIOVASCULAR STATES

CLAIM OF PRIORITY

This application claims priority to and benefit of U.S. Provisional Application Ser. No. 61/865,114 filed Aug. 12, 2013 entitled "Temporal Pattern-Based Hemodynamic Dysfunctional Detection and Intervention Guidance," the disclosure of which is incorporated herein by reference in its entirety.

BACKGROUND

The primary role of the cardiovascular system is to facilitate adequate circulating blood volume to provide sufficient oxygen delivery, thereby meeting the metabolic demands of the tissues and cells. The adequacy of circulating blood volume may be affected by the functional effectiveness of the cardiovascular system. A healthy cardiovascular system may be characterized, in part, by its ability to maintain adequate oxygenated blood flow and pressure in response to changes in the demand for oxygenated blood. Such changes may result from traumatic stresses or changes in the metabolic health of tissues or organs reflected in their ability to extract or use oxygenated blood. An impaired cardiovascular system may not be able to supply sufficient oxygen to tissues or adapt to circulatory stress. If oxygen delivery to tissue has been compromised, tissue hypoxia may occur. If tissue hypoxia is prolonged, acute cellular or organ damage may occur resulting in long term patient morbidity or mortality.

Cardiovascular impairment can occur due to sudden pathology or trauma, resulting in shock. Alternatively, such impairment may occur in resting patients due to underlying chronic pathologies, such as heart failure. Additionally, external volemic stressors, including some medical procedures, may cause fluid to transfer into or out of the arterial tree. As one example, ultrafiltration used for kidney replacement therapy may result in an induced hypovolemic condition due to a mismatch between the rate of volume removal from the vasculature and the rate of refill of fluid volume from outside of the vasculature. In another example, poor management of aquapheresis therapy for heart failure patients having cardiac pulmonary edema may also result in a significant change in patient fluid volume. Thus, a hypovolemic condition may be induced if too much fluid is removed, or residual edema may result if too little is removed. For patients undergoing surgery, the vasodilation effects of analgesics and paralytics may result in too little effective or maintained fluid volume. Alternatively, surgical patients may receive excess fluid volume from intravascular administration of normal saline solution.

While hemodynamic dysfunction conditions may be present in an acute care setting, the initial onset of such conditions may begin in other venues with or without the patient presenting any related symptoms. Some non-limiting examples of such non-acute care settings may include clinics, physician offices, nursing homes, pre-hospital emergent care transport facilities, transitional care facilities, and the home. It may be understood that accurate detection of pre-symptomatic or early symptomatic hemodynamic dysfunction by caregivers in these non-acute settings may permit the caregivers to intervene proactively, thereby avoiding a possible acute event or a least minimizing the adverse effects on the patient. Typically, only non-invasive medical device technologies are tolerated in such non-acute care settings. Additionally, caregivers at these facilities may not have sufficient or detailed medical training to recognize when a patient has a hemodynamically unstable condition, or to accurately diagnose the type of dysfunction and provide the necessary care.

SUMMARY

Before the present methods, systems and materials are described, it is to be understood that this disclosure is not limited to the particular methodologies, systems, and materials described, as these may vary. It is also to be understood that the terminology used in the description is for the purpose of describing the particular versions or embodiments only, and is not intended to limit the scope.

In an embodiment, a method for determining a cardiovascular state of a patient in a stress condition may include receiving, by a computing device, at least one signal in the time domain from at least one sensor in operative communication with the patient in a stress condition, in which the at least one signal in the time domain is a pulse wave measurement of the patient, determining, by the computing device, at least one metric in the frequency domain from the at least one signal in the time domain, and determining, by the computing device, the cardiovascular state of the patient from the at least one metric in the frequency domain and information from at least one database of cardiovascular states.

In an embodiment, a system for determining a cardiovascular state of a patient in a stress condition may include at least one sensor configured to received one or more signals from the patient, a computing device in data communication with the at least one sensor, a non-transitory, computer-readable storage medium in operable communication with the computing device, an input device in operable communication with the computing device, and an output device in operable communication with the computing device. Further, the computer-readable storage medium may contain one or more programming instructions that, when executed, cause the computing device to receive at least one signal in the time domain from the at least one sensor, in which the at least one signal in the time domain is a pulse wave measurement of the patient, determine at least one metric in the frequency domain from the at least one signal in the time domain, and determine the cardiovascular state of the patient from the at least one metric in the frequency domain and information from at least one database of cardiovascular states.

BRIEF DESCRIPTION OF THE DRAWINGS

FIG. 6C depicts an ECG trace and a pulse waveform trace in accordance with some embodiments.

FIG. 7 depicts, in tabulated form, information in a database of cardiovascular states in accordance with some embodiments.

DETAILED DESCRIPTION

A physiology monitoring system that employs one or more non-invasive measures to continuously assess a patient's physiology may include a computing system along with one or more patient sensors to derive metrics that, in conjunction with a database, can be used to recognize cardiovascular dysfunctional states.

A cardiovascular dysfunctional state can be in the form of inadequate global circulatory blood flow, inadequate circulatory blood volume, low tissue perfusion, local ischemia, or inappropriate tissue or cellular oxygen extraction or use due to metabolic dysfunction. In some instances, patients having multiple comorbidities can exhibit atypical physiological responses thereby causing hemodynamic dysfunction condition. For such patients, the patient monitoring system may further include strategies to enable detection of such atypical physiological responses to hemodynamic dysfunctions. For example, a measurement of systolic blood pressure less than 90 mm Hg, indicating hypotension, by itself may be an inadequate measure of cardiovascular status for a patient diagnosed with advanced cardiac disease. Additional data, such as the types and frequencies of occurrence of dysrhythmias—including bradycardia, tachycardia, and abnormal R-R dispersion—may improve the characterization of the patient's cardiovascular state, thereby leading to more effective treatment protocols.

As disclosed above, pre-symptomatic hemodynamic dysfunction may occur outside of critical care facilities. Such alternative care venues may lack sophisticated technology required to diagnose the specific dysfunction and provide appropriate care. In some instances, such alternative care venues may only have access to non-invasive patient monitoring equipment capable of providing only traditional vital signs. Such monitoring equipment may have poor sensitivity for detecting early stages of cardiovascular dysfunction as well as poor specificity regarding the underlying cardiovascular components that may contribute to this condition. Additionally, the personnel at such facilities may lack the specialized medical expertise needed to properly interpret the data from the monitoring equipment. It may be appreciated that such health care facilities and personnel may benefit from a physiology monitoring system adapted to receive data from such non-invasive sensors and provide an expert-like diagnosis of patient status that may be beyond the expertise of the local health care personnel.

Figure 1:
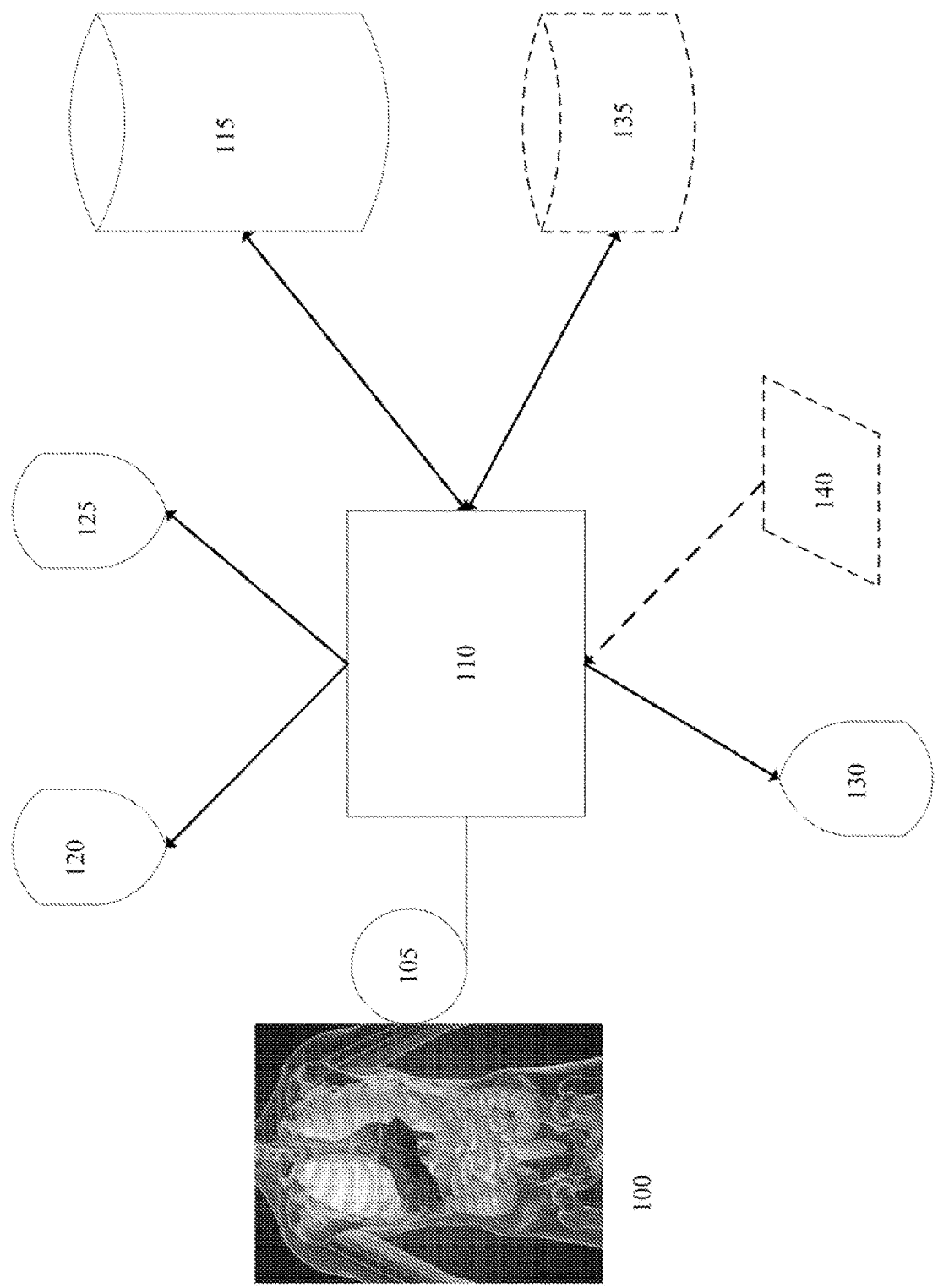
FIG. 1 depicts an illustrative model-based patient monitoring system in accordance with some embodiments.

An exemplary physiological monitoring system capable of providing expert-like diagnostic information regarding a patient status is depicted in FIG. 1. Such a system may generally include a computing device 110 having one or more interfaces to receive time domain physiological sensing signals from each of one or more physiological sensors 105 associated with a patient 100. The monitoring system may also contain, or be in communication with, one or more databases 115, 135 containing information related to one or more patient conditions or states. The computing device 110 may transform the one or more time sensing signals into one or more frequency domain metrics that may be compared to the information contained in the one or more databases 115, 135. Based on the comparison, the computing device 110 may provide one or more outputs 120, 125, 130 to be received by the patient or one or more health care providers (hereafter, "user").

In some non-limiting applications, the computing device 110 may simply monitor the one or more physiological signals from the patient 100 and provide the user with an output 120 including updated information regarding the one or more time domain sensing signals, one or more derived time domain metrics, or one or more derived frequency domain metrics. It may be appreciated that additional information related to the patient condition and environment may also be displayed including, without limitation, patient blood pressure, patient temperature, and current date and time. Such monitoring capabilities may be also be used for assessing the cardiovascular health of a patient in a normative state, such as an elderly patient having an age-related decrease in vascular reserve but who is otherwise healthy. Cardiovascular monitoring may also be useful as part of a sports-training program to determine the effectiveness of an athlete's training program.

In another non-limiting application, the computing device 110 may monitor the one or more time domain sensing signals from the patient 100, provide one or more derived time domain metrics or frequency domain metrics therefrom, and provide the user with an output 125 including one or more warning indicators of an emergent patient condition, such as being pre-symptomatic for a hemodynamic dysfunction condition. Such warning indicators may be based on one or more of the one or more time domain sensing signals, one or more derived time domain metrics, one or more related frequency domain metrics, and information obtained from a database of cardiovascular states 115. Warning indicators for notification of a user may include, without limitation, one or more of an audible alarm, a visual indicium on a computing device display, and a text message to a mobile communication device.

In still another non-limiting application, the computing device 110 may monitor the one or more time domain sensing signals from the patient 100, derive one or more time domain metrics and/or frequency domain metrics therefrom, and provide the user with an output 130 related to one or more proposed standardized therapeutic protocols appropriate to the patient's 100 cardiovascular status. Such therapeutic recommendations may be based on the one or more time domain sensing signals, one or more time domain and/or frequency domain metrics derived from the time domain signals, information obtained from a database of cardiovascular states 115, and additional information from a database of therapeutic protocols 135.

In yet another alternative application, the computing device 110 may monitor the one or more time domain sensing signals from the patient 100, derive one or more time domain metrics and/or frequency domain metrics therefrom, and provide the user with an output 130 related to one or more changes to a standardized therapeutic protocol based on one or more of the one or more time domain sensing signals, one or more derived time domain metrics, one or more derived frequency domain metrics, information obtained from a database of cardiovascular states 115, information from a database of therapeutic procedures 135, the patient's 100 medical history information 140, and additional patient medical status information. Non-limiting examples of such patient medical status may include one or more of an indicator of the patient's age, an indicator of the patient's body mass, an indicator of the patient's gender, an indicator of one or more patient co-morbidities, an indicator of one or more patient medications, an indicator of the dosage of each of the one or more patient medications, an indicator of one or more patient therapies, an indicator of one or more patient surgeries, and an indicator of one or more patient genetic predispositions to one or more pathologies.

In some non-limiting examples, the one or more sensors 105 may include a transmittance photo-optic sensor, a reflective photo-optic sensor, a pressure transducer, a tonometry device, a strain gauge, an ultrasound device, an electrical impedance measurement device, and a radar device. Additional sensors 105 may include a blood pressure measurement device, a plethysmograph, and an electro-cardiograph device (ECG). It may be understood that the one or more sensors 105 may be in physical contact with a surface of the patient or disposed within a natural cavity of the patient, such as the mouth, ear canal, rectum, or vagina. Alternative sensors 105 may be remotely placed with respect to the patient's body and lack physical contact with the patient.

Examples of time domain signals that may be obtained by the computing device 110 from such sensors 105 may include a pulse volume waveform, a pulse pressure waveform, a measurement of red blood density, an indicator of circulatory blood flow, a measure of arterial blood pressure, a measurement of cardiac electrophysiology, a measurement of vascular compliance, a measurement of specific muscle tissue oxygenation, and time-dependent changes in total fluid volume. Such time domain signals may be representative of one or more of a patient's cardiac function, a patient's respiration function, and the compliance of the patient's vasculature. The one or more time domain signals may be received by the computing device from the patient experiencing one or more of an injury, a pathological process, a surgical procedure, a diagnostic procedure, a therapeutic procedure, and a result of a genetic pre-disposition. Non-limiting examples of pathological processes may include one or more of cardiac myopathy, chronic obstructive pulmonary disease, chronic venous insufficiency, and renal failure. Non-limiting examples of a surgical procedure may include any surgical procedure requiring the use of an anesthesia agent, such as one or more of a cardiac surgery, a vascular surgery, a pulmonary surgery, a renal surgery, an abdominal surgery, and a cranial surgery. Non-limiting examples of a therapeutic procedure may include any therapeutic procedure to treat one or more components of the cardiovascular system, such as a dialysis procedure, a cardiovascular rehabilitation procedure, a skeletal muscle rehabilitation procedure, and an aquapheresis procedure. Non-limiting examples of a diagnostic procedure may include one or more cardiovascular reflex tests, including a cardiac function assessment procedure, a vascular non-compliance assessment procedure, a tissue edema assessment procedure, and a pulmonary edema assessment procedure.

Additionally, time domain signals may be obtained from a patient in a normative or near-normative condition (for example, during rest or during a time period prior to or after a surgical, therapeutic, or diagnostic procedure). Such signals, obtained under normative patient conditions, may provide baseline information regarding the patient's status for comparison to a status of the patient in a stressed state.

Figure 2:
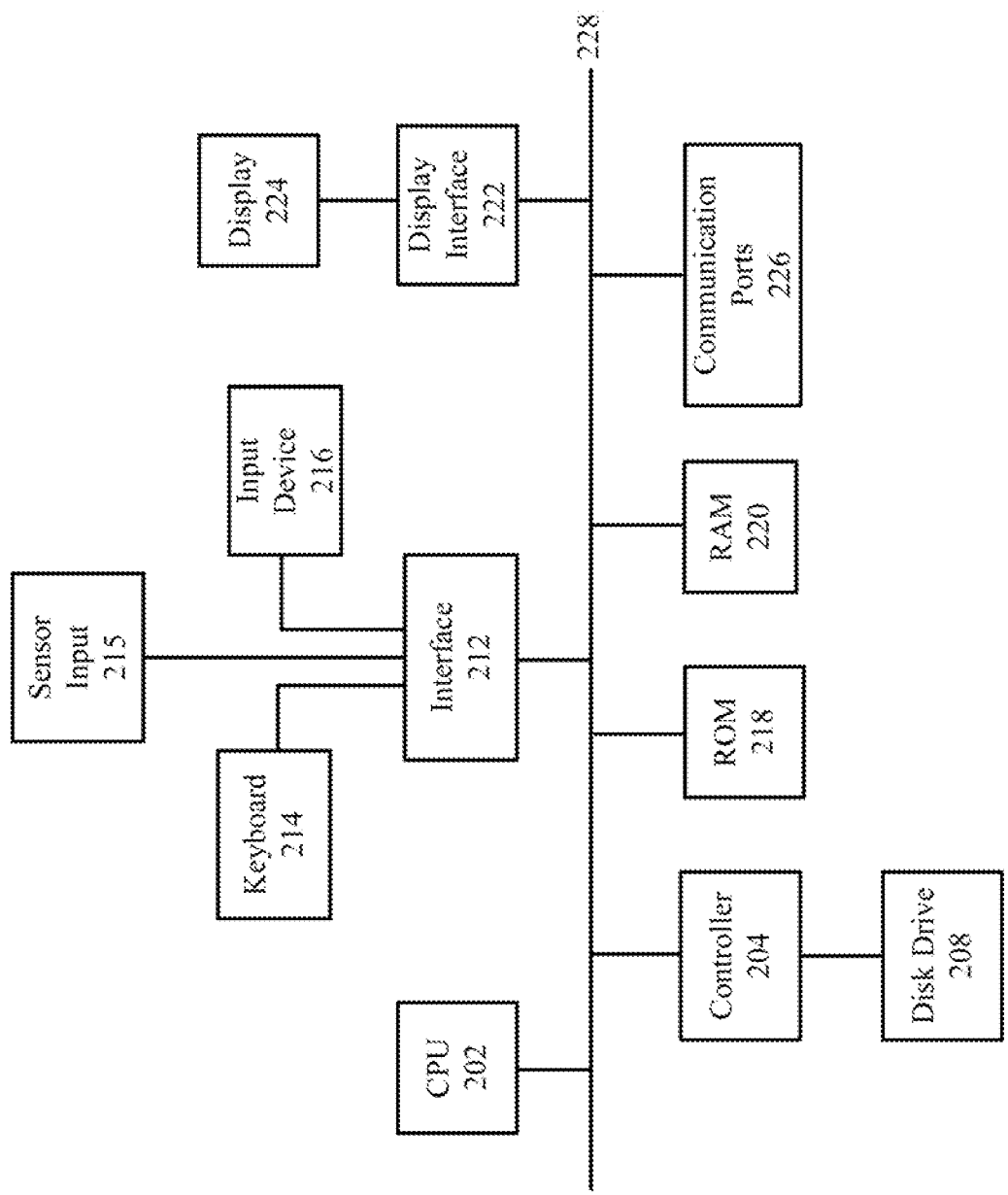
FIG. 2 depicts a computing device that may be used with the patient monitoring system in accordance with some embodiments.
Figure 3:
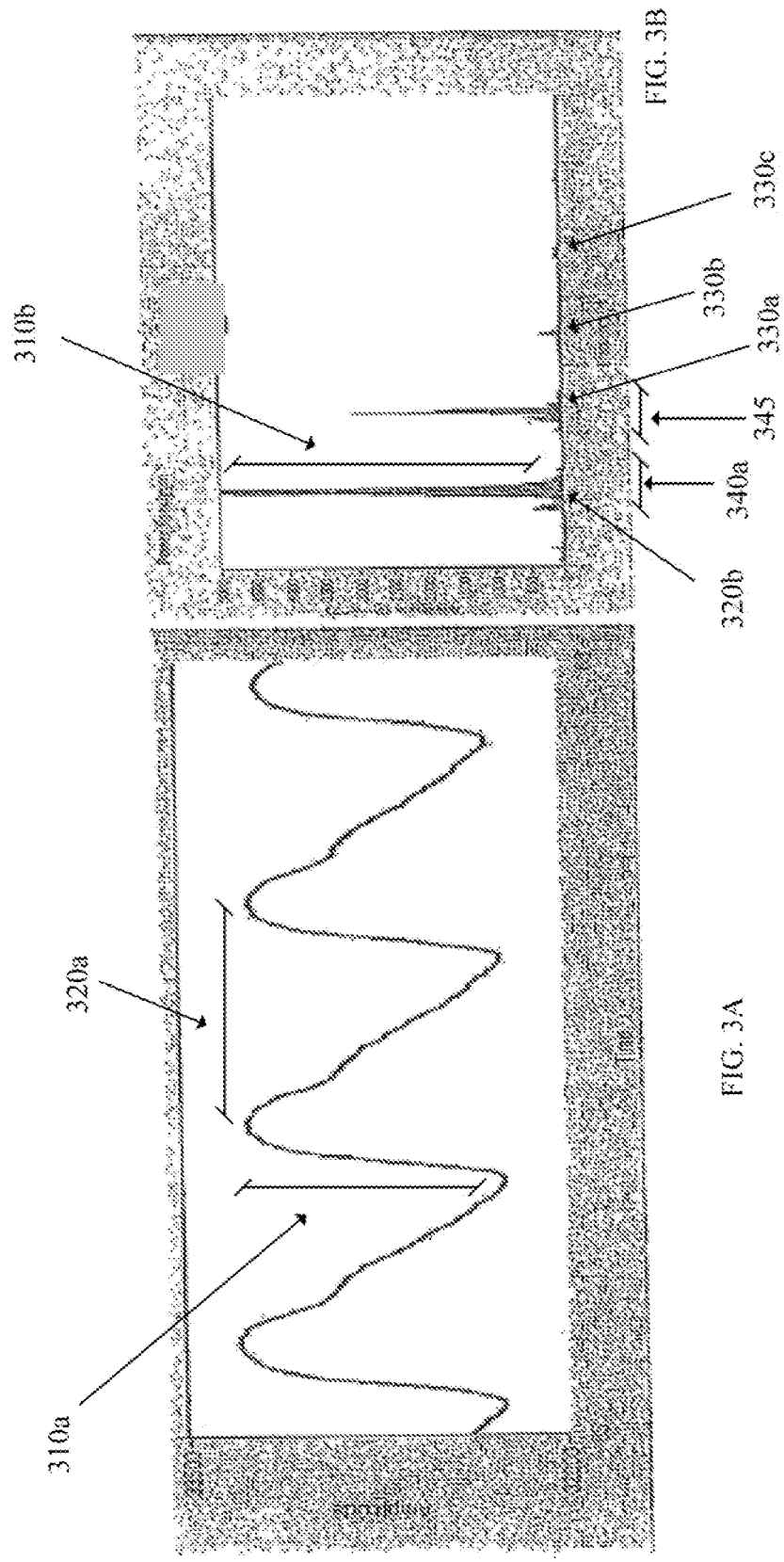
FIGS. 3A and 3B depict a pulse wave signal in the time domain and a frequency domain signal derived therefrom, respectively, in accordance with some embodiments.

FIG. 2 depicts a non-limiting example of a computing device that may be incorporated into a physiology monitoring system. Such a computing device may incorporate one or more of the following components. It may be appreciated that additional components not disclosed below, but which may be components of computerized systems known in the art, may also be included. The number or types of such components may vary, such as more than one central processing unit or bus. The data connectivity among the devices also may not be limited to the data connectivity as disclosed below. Additional computing, communications, input interfaces, and output interfaces beyond those disclosed below may also be considered incorporated into such a computing device.

A bus 228 may serve as the main information highway interconnecting the other illustrated components of the hardware. A CPU 202 is the central processing unit of the system, performing calculations and logic operations required to execute a program. Read only memory (ROM) 218 is one example of a static or non-transitory memory device, and random access memory (RAM) 220 is one example of a transitory or dynamic memory device.

A controller 204 may interface the system bus 228 with one or more optional disk drives 208. These disk drives 208 may include, for example, external or internal DVD drives, CD ROM drives, or hard drives.

Program instructions, as well as one or more databases, may be stored in the ROM 218 and/or the RAM 220 or other memory storage device associated with the computing device. Optionally, program instructions or one or more databases may be stored on a computer readable storage medium such as a compact disk or a digital disk or other recording medium, a communications signal, or a carrier wave. Additionally, program instructions, or other data—for example, one or more databases—may be stored on one or more removable memory devices that may include, as non-limiting examples, one or more removable discs, one or more removable cards, one or more removable memory sticks, one or more flash drives, one or more removable SIM chips, one or more writable CD ROMs or DVD disks, and/or one or more miniature data tapes. Such devices may also be used to transfer data from the computing device to another data receiving device such as a home computer. The computing device may also include stored records of the patient's status over time in any of its storage or memory devices including, without limitation, the ROM 218, RAM 220, disk drives 208, or removable storage media as disclosed above. Such patient-specific data may also be accessible over any data communication interface with additional storage devices, such as servers and data-farms. The computing device may also store event trends of the patient in its storage or memory devices, or store such data in a point-of-care data facility or in a remotely accessible data repository.

An optional display interface 222 may permit information from the bus 228 to be displayed on one or more display devices 224 in audio, graphic, or alphanumeric format. Additional output interface devices may include a monitor a flat-screen display, an LCD panel device, a touch screen device, an audio device, an LED device, a data communications link to a remote output or display device, and a haptic device. Communication with external devices may occur using one or more communication ports 226. The one or more communication ports 226 may be configured to act as data communication links to additional computing devices, communication devices, telephony devices, networks, and data repositories or servers. In some non-limiting examples, the one or more data communication links may include one or more of an internet connection, a wireless connection, a telephonic connection, a LAN connection, a WAN connection, and a personal area network. It be recognized that computer instructions, patient medical history data, and one or more databases may be contained in a memory storage device accessible to the computing device over such a data communication link.

Additionally, the computing device may display information at a point-of-care location, a central care delivery location such as at a nurse's station, or at a remote location. Such information may be related to adverse or emergent events associated with changes in hemodynamic, cardiovascular, and/or volumetric status of the patient. In some non-limiting examples, such information may include a notification of emergent events including one or more of an audible signal, a visual signal on a display, and a text message to a mobile communication device. Visual signals may include, without limitations, indicia on a graphical output on a computer screen (such as arrows to indicate features of importance), texts on a graphical output, and lighted displays such as light bulbs, LEDs and other sources of visual information that may not be associated with a particular computer screen or monitor.

In addition to the components disclosed above, the hardware may also include one or more interfaces 212 which may allow for receipt of data from one or more input devices 216 such as a keyboard 214, a touch screen, a mouse, remote control, pointing device, pushbutton, haptic device, a voice recognition device, and/or a joystick. An input device 216 may also include one or more of a removable memory device and a data communication link to a remote device configured to provide input data to the computing device. The one or more interfaces 212 may also receive time domain physiological signals from the one or more physiological sensors via one or more sensor inputs 215.

FIGS. 3A-6B depict several examples of time domain signals acquired by the computing device, as well as time domain metrics and frequency domain metrics that may be determined or calculated by the computing device.

FIGS. 3A and 3B depict a trace of a pulse volume waveform (time domain) and a power spectrum analysis (frequency domain) of the same waveform, respectively. In some non-limiting examples, the time domain signal may be transformed into a frequency domain signal by means of a Fourier transform algorithm. The pulse volume waveforms in FIG. 3A may be characterized by one or more metrics in the time domain. Examples of such time domain metrics may include peak amplitudes 310a and differences in occurrence times 320a between successive waveform peaks. It may be understood that the pulse volume waveforms in FIG. 3A may correspond to data received in the time domain from a pulse volume sensor such as a photoplethysmograph.

The power spectrum graph in FIG. 3B may be characterized by one or more metrics in the frequency domain. Non-limiting examples of such frequency domain metrics may include a fundamental frequency 320b of the at least one signal in the time domain, a frequency 330a,b,c of one or more integer harmonics of the at least one signal, a phase value of the fundamental frequency 320b, a phase value at a frequency 330a,b,c of the one or more integer harmonics of the at least one signal, a frequency change in the fundamental frequency 320b, a frequency change in one or more frequencies 330a,b,c of the one or more integer harmonics, a phase change in the fundamental frequency 320b, a phase change in one or more frequencies 330a,b,c of the one or more integer harmonics, a power amplitude 310b at the fundamental frequency of the at least one signal in the time domain, a power amplitude at each frequency of the one or more integer harmonics of the at least one signal in the time domain, a frequency dispersion about the fundamental frequency of the at least one signal, and a frequency dispersion about the frequency of the one or more integer harmonics of the at least one signal. It may be recognized that frequency dispersion values may be determined from the fine structure 340a associated with the fundamental frequency 320b or the fine structure associated with each of the integer harmonics (such as the fine structure 345 about the first integer harmonic peak 330a). In some non-limiting examples, the fundamental frequency 320b may be the fundamental frequency corresponding to a heart rate.

More complex frequency domain metrics may also be calculated from a frequency domain analysis of the one or more time domain sensing signals. Thus, in some non-limiting examples, one or more metrics in the frequency domain may be calculated by the computing device by transforming the one or more signals in the time domain into one or more signals in the frequency domain, selecting at least one frequency domain feature of the one or more signals in the frequency domain, and normalizing the one or more frequency domain features to one or more frequency domain feature baseline values.

Some non-limiting examples of frequency domain features that may be normalized to calculate frequency domain metrics may include a fundamental frequency 320b, a frequency 330a,b,c of one or more integer harmonics of the fundamental frequency, a phase value of the fundamental frequency 320b, a phase value at a frequency 330a,b,c of the one or more integer harmonics of the at least one signal, a frequency change in the fundamental frequency 320b, a frequency change in one or more frequencies 330a,b,c of the one or more integer harmonics, a phase change in the fundamental frequency 320b, a phase change in one or more frequencies 330a,b,c of the one or more integer harmonics, a power 310b at the fundamental frequency, a power at the frequency 330a,b,c of the one or more integer harmonics of the fundamental frequency, a change in the fundamental frequency 320b, a change in the frequency 330a,b,c of the one or more integer harmonics, a frequency of one or more sidebands of the fundamental frequency, a power at the frequency of the one or more sidebands of the fundamental frequency, a dispersion of frequencies about the fundamental frequency, a dispersion of frequencies about the one or more integer harmonics of the fundamental frequency, a measure of harmonic distortion, and a dispersion of frequencies within one or more sidebands of the fundamental frequency.

It may be understood by one having ordinary skill in the art of signal analysis that integer harmonics of a fundamental frequency constitute frequency components at integer multiples of the fundamental frequency. Side-band frequencies, however, may be understood to be frequency components arising from the admixture of two frequencies, $f_1$ and $f_2$ (wherein $f_1 > f_2$) in which the side-bands appear at frequencies $f_1 - f_2$ and $f_1 + f_2$. Such frequency admixture may occur, for example, due to admixture of respiratory frequencies with cardiac frequencies.

Some non-limiting examples of frequency domain feature baseline values may include one or more average values of the frequency domain feature of the patient over time, a maximum value of the frequency domain feature of the patient over time, an average value of the frequency domain feature from a plurality of patients, a maximum value of the frequency domain feature from the plurality of patients, an average value of the frequency domain feature of the patient not in a stress condition, and a maximum value of the frequency domain feature of the patient not in a stress condition.

In some non-limiting examples, normalizing the one or more frequency domain features to one or more frequency domain feature baseline values may include dividing, by the computing device, the one or more frequency domain feature values by the one or more frequency domain feature baseline values. In another non-limiting example, normalizing the one or more frequency domain features to at least one frequency domain feature baseline may include subtracting one or more frequency domain feature baseline values from the one or more frequency domain feature values to yield one or more numerators, and dividing the one or more numerators by the one or more frequency domain feature baseline values.

Figure 4:
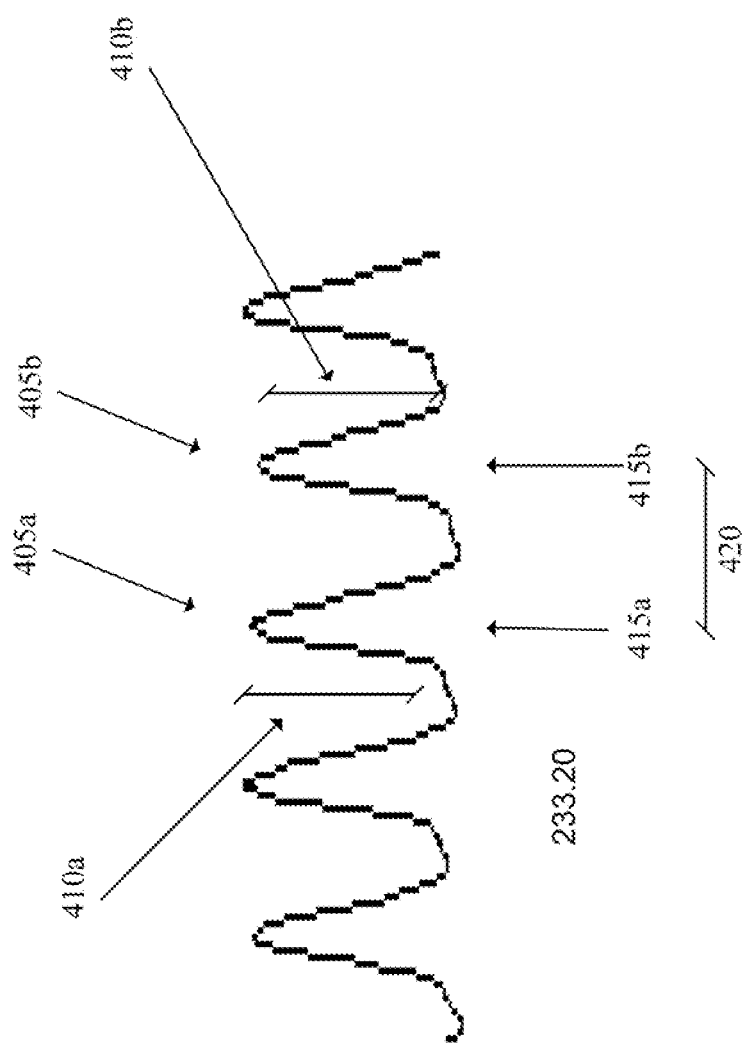
FIG. 4 depicts metrics associated with a pulse wave signal in the time domain in accordance with some embodiments.

FIG. 4 depicts an example of features that may be obtained from a time domain pulse wave signal. The pulse wave signal may be characterized by one or more peaks 405$a,b$, each peak characterized by a peak amplitude 410$a,b$ (respectively) and a peak occurrence time 415$a,b$ (respectively). In some embodiments, a time domain metric may be calculated from a plurality of time difference values 420. In other embodiments, a time domain metric may be calculated from a difference in the amplitude values 410$a,b$ of successive peaks 405$a,b$ (respectively). Additional metrics in the time domain may include one or more of a signal peak amplitude value 410$a,b$ of the at least one signal in the time domain, an average of a plurality of signal peak amplitude values of the one or more signals in the time domain obtained within a specified time window, a time difference 420 between an occurrence time 415$a$ of a first signal peak and of a second signal peak 415$b$ of the one or more signals in the time domain, a dispersion of a plurality of signal peak amplitude values of one or more signals in the time domain, and a dispersion of a plurality of time differences between an occurrence time of a first signal peak and a second signal peak of the one or more signals in the time domain.

More complex time domain metrics may also be calculated from features derived from the one or more time domain sensing signals. Thus, in some non-limiting examples, one or more metrics in the time domain may be calculated by the computing device by selecting at least one time domain feature of the one or more signals in the time domain, and normalizing the one or more time domain features to one or more time domain feature baseline values.

Some non-limiting examples of time domain feature baseline values may include one or more average values of the time domain feature of the patient over time, a maximum value of the time domain feature of the patient over time, an average value of the time domain feature from a plurality of patients, a maximum value of the time domain feature from the plurality of patients, an average value of the time domain feature of the patient not in a stress condition, and a maximum value of the time domain feature of the patient not in a stress condition In some non-limiting examples, normalizing the one or more time domain features to one or more time domain feature baseline values may include dividing, by the computing device, the one or more time domain feature values by the one or more time domain feature baseline values. In another non-limiting example, normalizing the one or more time domain features to at least one time domain feature baseline may include subtracting one or more time domain feature baseline values from the one or more time domain feature values to yield one or more numerators, and dividing the one or more numerators by the one or more time domain feature baseline values.

Additional metrics may include an analysis of the sensor signal morphology such as the appearance of multiple peaks or overlapping peaks in a pulse wave signal, or apparent grouping of peaks within one or more time windows. Characterization of morphology changes may also be performed in the frequency domain, including, without limitation, changes in phase metrics, or changes in one or more features of the frequency spectra.

Figure 5A:
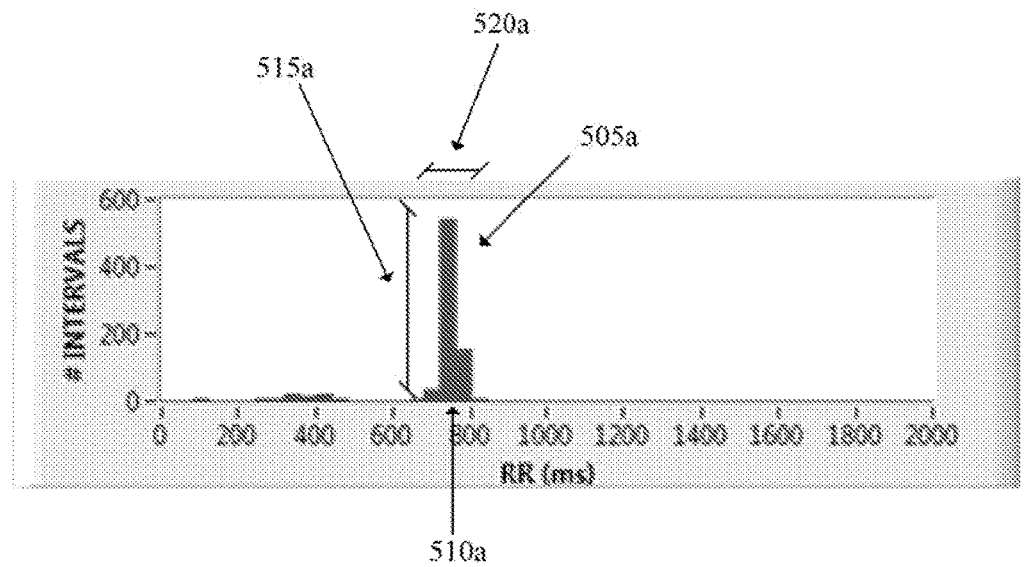
FIGS. 5A and 5B depict dispersion graphs of inter-peak occurrence times of a pulse wave signal in accordance with some embodiments.
Figure 5B:
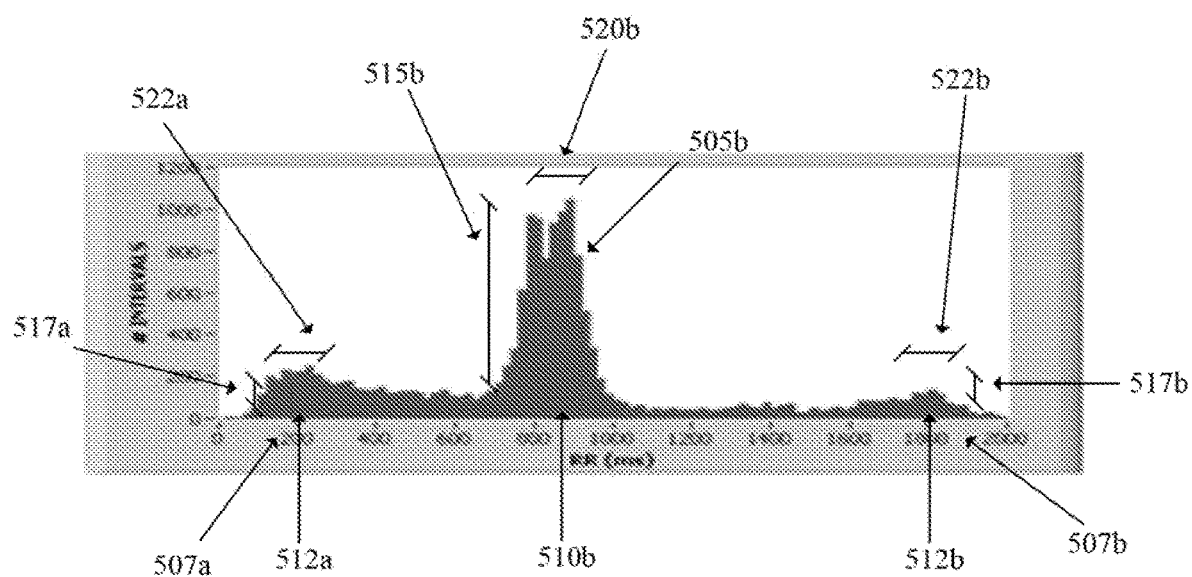

FIGS. 5A and 5B depict dispersion graphs of time differences between the occurrence times of successive peaks of a pulse wave signal. In some embodiments, such dispersion graphs may take the form of one or more histograms. A number of time domain metrics may be derived from such dispersion graphs. FIG. 5A illustrates a dispersion graph of time differences between successive pulse waveform peaks for a patient showing normative (typical or non-pathological) electrocardiac behavior. The dispersion graph in FIG. 5A may be characterized by a narrow primary peak 505$a$ centered around a primary time difference 510$a$ of about 750 msec. The primary peak 505$a$ may represent a normal pulse time (reciprocal pulse rate) corresponding to a pulse rate of about 80 bpm (beats per minute). The primary peak 505$a$ may be characterized by any number of dispersion metrics including, for example, a primary time difference 510$a$ and a primary amplitude 515$a$. The primary peak 505$a$ may also be characterized by a primary peak width 520$a$. A dispersion graph peak width metric may be calculated according to any method known to one skilled in the art including, without limitation, a half-width at half-maximum (HWHM) or a full-width at half-maximum (FWHM). More complex metrics for the width of the dispersion graph peak may be derived from a fit of the peak to a known curve (such as a Gaussian function) having known parameters associated with the curve spread (such as a Guassian function a parameter).

FIG. 5B illustrates a dispersion graph of time differences between successive pulse waveform peaks for a patient having multifocal premature ventricular beats. The dispersion graph in FIG. 5B may be characterized by a symmetric primary peak 505$b$ centered around a primary time difference 510$b$ of about 900 msec along with two secondary peaks 507$a,b$ centered around secondary time differences 512$a,b$ of about 200 msec and about 1800 msec, respectively. The primary peak 505$b$ may be characterized by any number of dispersion metrics including, for example, a primary time difference 510$b$ and a primary amplitude 515$b$. The primary peak 505$b$ may also be characterized by a primary peak width 520$b$. In FIG. 5B, it may be observed that the two secondary peaks 507$a,b$ do not appear to be symmetric based on their respective secondary peak widths 522$a,b$. The two secondary peaks 507$a,b$ may be characterized by any number of dispersion metrics including, for example, secondary time differences 512$a,b$ (respectively) and secondary amplitudes 517$a,b$ (respectively). Although a dispersion graph peak width metric associated with the primary peak width 520$b$ may be readily described by a single value, such as HWHM or FWHM, a more complex description of a dispersion graph peak width metric for the two secondary peaks 517$a,b$ may be required based on the asymmetry of their respective widths 522$a,b$.

As disclosed above, additional time domain sensing signals may be received by the computing device and used with one or more databases to classify a patient cardiovascular state, monitor a patient medical status, provide a user with notifications of pre-symptomatic cardiovascular events, and recommend therapies to mitigate the occurrence of such events. Such additional time domain signals may include, without limitation, time domain signals associated with patient respiration and time domain signals associated with cardiac electrical propagation events.

Figure 6A:
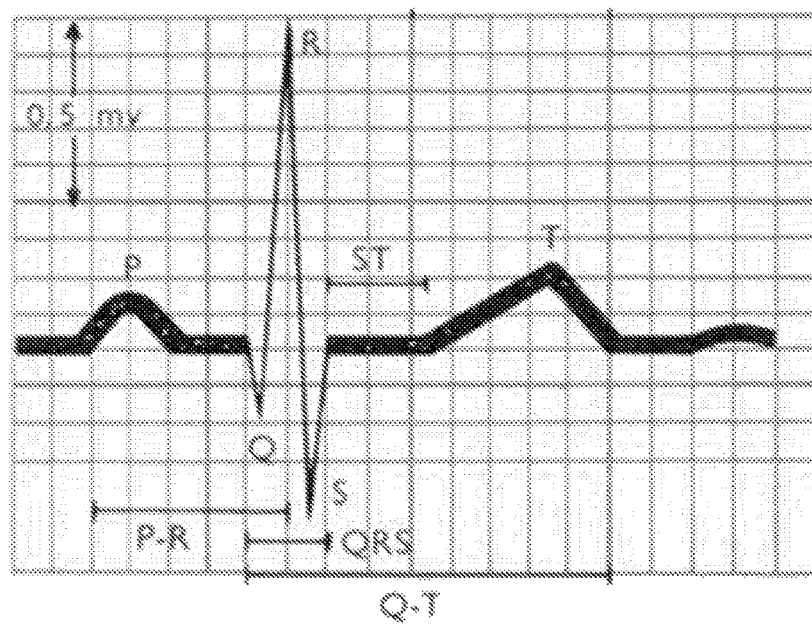
FIGS. 6A and 6B depict ECG traces in accordance with some embodiments.
Figure 6B:
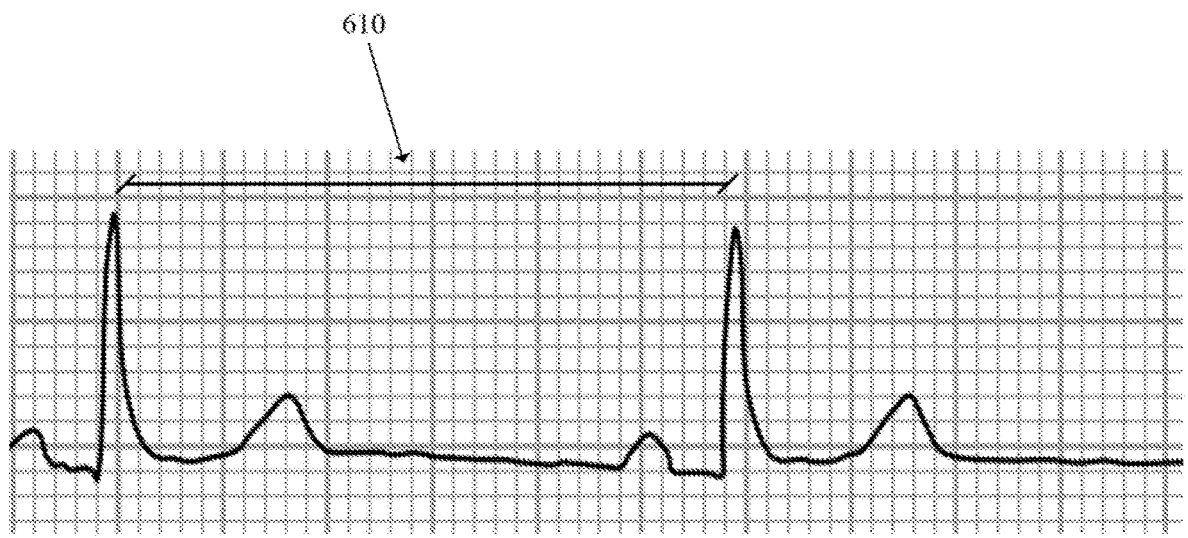

FIGS. 6A and 6B depict electrocardiograph (ECG) traces illustrating features often used by health care providers to assess the nature of cardiac contractility. Such ECG signals may also constitute time domain physiological signals received by the monitoring device. The ECG trace is frequently described in terms of the PQRST features, as indicated in FIG. 6A. The P feature generally corresponds to the depolarization of the atria of the heart, and is typically initiated at the sinoatrial node. The QRS complex typically corresponds to ventricular depolarization and typically is initiated at the atrioventricular node. The P-R time interval generally represents an electrical conduction time lag between the onset of atrial contraction and the onset of ventricular contraction. The Q-R time interval generally is the total time required for complete ventricular electrical depolarization and hence ventricular contraction. The T feature corresponds to the repolarization of the ventricular tissue, and the S-T interval is a lag time between ventricular depolarization and the onset of ventricular re-polarization. Other features may be found in an abnormal ECG depending on the pathology. Not shown in FIG. 6A is an R-R interval that generally corresponds to the time between successive ventricular contractions. For a normally functioning heart, the R-R interval is associated with the heart rate.

FIG. 6B illustrates an ECG trace characteristic of bradycardia. In FIG. 6B, two PQRST features may be observed. Although the PQRST features in FIG. 6B appear superficially the same as depicted in FIG. 6A, the R-R interval 610 appears significantly longer than may be found in normative heart rhythms. Typically, a resting heart rate may be about 50 bpm (beats per minute) to about 60 bpm, providing an R-R interval of about 1000 msec to about 1200 msec. It may be understood that athletically trained individuals may display unusually long R-R intervals, such as about 2200 msec. Clinically, however, a waking heart beat below 40 bpm (R-R interval greater than or about 1500 msec) is frequently considered pathological.

It may be understood that additional metrics in the time domain may be derived from the morphology of one or more ECG traces. Such metrics may provide indications of cardiopathologies including, but not limited to, premature ventricular contraction, tachycardia, bradycardia, atrial or ventricular fibrillation, re-entrant ventricular stimulation, and AV node dysrhythmias. As a non-limiting example, FIG. 6C depicts an ECG trace 630 showing both normal 635*a,b* and abnormal 637 ECG waveforms. Morphological ECG metrics in the time domain may be used to distinguish the normal 635*a,b* ECG waveforms from a waveform showing abnormal 637 structures, such as those consistent with quadrigeminy. It may also be noted that morphological anomalies found in ECG waveforms may be present as related anomalies in a pulse waveform. As additionally depicted in FIG. 6C, a pulse waveform 640 obtained at the same time as the ECG trace 630 illustrates normal 640*a,b* and abnormal 647 waveforms. Morphological pulse waveforms metrics in the time domain may also be used to classify or monitor a patient's cardiovascular state.

As disclosed above, the physiological monitoring system may acquire one or more time domain sensing signals and derive one or more time domain metrics and/or one or more frequency domain metrics therefrom. The system may also use information obtained from one or more databases to determine cardiovascular events either in a pre-symptomatic or symptomatic patient, or recommend one or more standard therapeutic protocols or modifications to therapeutic protocols to mitigate such events. Non-limiting examples of such databases may include a database of cardiovascular states, a database of therapeutic procedures or protocols, and a database comprising the patient's medical history. It may be understood that such databases may take on any format known to one having ordinary skill in the art, including, without limitations, tables, spreadsheets, linked lists, and relational databases. Similarly, one having ordinary skill in the art would understand that the system may use, without limitation, one or more of comparative methods, statistical methods, structured query methods, and sorting methods on the one or more databases in concert with the signals and/or metrics to obtain relevant system outputs for a user.

In some non-limiting embodiments, a database of cardiovascular states may contain information obtained from the patient being monitored or a plurality of patients. In some non-limiting embodiments, the information in the database of cardiovascular states may include one or more cardiovascular states for the patient being monitored or each of the plurality of patients from whom the information has been obtained. In some other non-limiting embodiments, the information in the database of cardiovascular states may include one or more metrics in the frequency domain and/or one or more metrics in the time domain derived from one or more signals in the time domain from the patient being monitored or from each of the plurality of patients from whom the information has been obtained. Examples of such a time domain signal may include a pulse wave measurement from the patient being monitored or from each of the plurality of patients from whom the information has been obtained. Additionally, the information in the database of cardiovascular states may include one or more indicators of a medical status of the patient being monitored or each of the plurality of patients from whom the information has been obtained.

The cardiovascular states included in the one or more databases may include any descriptor of a patient state, including, without limitation, an obstructive sleep disorder state, an anesthesia-induced hypovolemia state, a hemodialysis-induced hypovolemia state, and a hemodialysis-induced tissue low perfusion state of a patient having heart failure. It may be recognized that other states may be related to patient responses to pathologies, surgeries, therapeutic procedures, and diagnostic procedures. In some additional examples, the databases may include sub-groupings of states under more general states. Such sub-groups, for example, may be used to further classify a patient according to an indication of severity of the state or an indication of the length of time the patient has been classified as being within the state.

In addition to a set of cardiovascular states, the one or more databases may contain one or more sets of parameters that may be associated with each of the states. Such parameters may be derived from values of one or more metrics in the frequency domain and/or time domain.

In one non-limiting example, the one or more sets of parameters may include one or more set of ranges of the one or more metrics, either as signed values or absolute values. Values of time domain and/or frequency domain metrics obtained from a patient may be compared to such ranges in parameter values. If a metric value is encompassed within a parameter value range, the metric may be considered "positive" for that parameter. In some instances, cardiovascular states may be subdivided into sub-states encompassing narrower parameter ranges within a larger parameter range of the original state. A patient may thus be classified among such subgroups based on the subrange of values within which the patient's data falls.

In another non-limiting example, the one or more sets of parameters may include one or more sets of temporal variations (trends or temporal patterns) of the one or more metrics over some specified time window of observation. Temporal variations in values of time domain and/or frequency domain metrics obtained from a patient may be compared to such temporal variation values. If a metric value shows a temporal variation within a parameter trend or temporal pattern within the specified time window, the metric may be considered "positive" for that parameter. In some instances, cardiovascular states may be subdivided into sub-states encompassing degrees of temporal variations. Thus, a sub-state may have an increasing temporal variation having endpoints within the total group temporal variation of the original state.

In another non-limiting example, the one or more sets of parameters may include one or more sets of averages or other statistics (such as measures of the variation) of the one or more metrics.

In yet another non-limiting example, the one or more sets of parameters may include one or more sets of threshold values of the one or more metrics. In one embodiment, if a metric value shows a value greater than a parameter threshold (depending on the metric), the metric may be considered "positive" for that parameter. In another embodiment, if a metric value shows a value less than a parameter threshold (depending on the metric), the metric may be considered "positive" for that parameter. Such threshold values may include average values, maximal values, or other values that can be used to characterize each of the states or subgroup of states.

It may be understood that the database of cardiovascular states may be updated at any time. Such updates may include one or more updates to the states already incorporated in the database, additions of new states to the database, and subdivisions of states into sub-states. Values for parameters may also be updated, added, or changed as required. In some examples, an updated database may be loaded into a memory component of the physiological monitoring device. In another example, an updated database may be loaded into a remote device, such as a server, in data communication with the physiological monitoring device. In still another example, an updated database may be created by the physiological monitoring device by adding monitored patient data including one or more of the signals in the time domain, one or more metrics in the frequency domain, and one or more metrics in the time domain derived from one or more sensing signals obtained from the patient under monitoring conditions. In addition, the physiological monitoring system may calculate, correlate, or otherwise determine one or more sets of parameters from the one or more of the signals in the time domain, one or more metrics in the frequency domain, and one or more metrics in the time domain derived from one or more sensing signals obtained from the patient under monitoring conditions. In some non-limiting examples, the cardiovascular state of a patient may be updated during a monitoring session based on the updated information in the database of cardiovascular states.

FIG. 7 depicts data that may be included in a database of cardiovascular states. The left-hand column in FIG. 7 presents potential cardiovascular states of a patient. The top row in FIG. 7 is a header row of parameters that may be relevant to classifying a patient among the cardiovascular states. The entries in FIG. 7 are graphical representations of temporal variations of the parameters that may be correlated with the classes of states. Thus, a single up-arrow (↑) may represent an increase in a parameter value over time and a single down-arrow (↓) may represent a decrease in a parameter value over time. A doubled up-arrow (↑↑) or down-arrow (↓↓) may represent a sudden or large change in a parameter value over time (increase and decrease, respectively). In some instances, a change in a parameter value may not be correlated or associated with a particular state (denoted by "x"). It may be understood that the database of cardiovascular states may include values of parameters to characterize the states as disclosed above.

In addition to a database of cardiovascular states, the physiological monitoring device may also contain in a memory component or have access to one or more of a database of therapeutic protocols and a database of patient medical histories. A database of therapeutic protocols may include any of the information in the database of cardiovascular states along with one or more descriptors of standardized protocols for mitigating cardiovascular pathologies associated with the cardiovascular states. Such therapeutic protocols may include one or more of a pharmaceutical intervention, a surgical intervention, a diuresis intervention, or an electrical intervention. Pharmaceutical interventions may include the administration of inotropic drugs or vasoactive drugs according to standardized dosing schedules. Electrical interventions may include the use of an implantable cardiac pacemaker or muscular electro-stimulator. A therapeutic database may additionally include parameter settings to be provided to devices used in therapeutic procedures, for example parameters to be used with a diuresis device to optimize the removal of fluid from a patient. A therapeutic database may further include ratings of therapeutic protocol effectiveness for each of the cardiovascular states.

A database of patient medical histories may include any of the information in the database of cardiovascular states along with one or more descriptors related to a patient's medical history. Such indicators may include one or more of an indicator of a patient age, an indicator of a patient body mass, an indicator of a patient gender, an indicator of one or more patient co-morbidities, an indicator of one or more patient medications, an indicator of a dosage of each of the one or more patient medications, an indicator of one or more patient therapies, an indicator of one or more patient surgeries, and an indicator of one or more patient genetic predispositions to one or more pathologies.

Additionally, a physiological monitoring system may be used to construct one or more databases including sets of patient cardiovascular states and parameters derived from sensing signals from patients under monitoring conditions. Thus, common patient temporal patterns of response may be correlated to static patient data, common intervention strategies, or parameter settings applied to a machine used in the performance of the intervention. The physiological monitoring system may include analysis capabilities to statistically correlate temporal patterns of sensor data, time domain metrics, and frequency domain metrics to determine parameter ranges, averages, or threshold values to incorporate into the one or more databases. Such a monitoring system may also include patient symptom data and medical history data as part of the pattern of response in a database repository.

Figure 8:
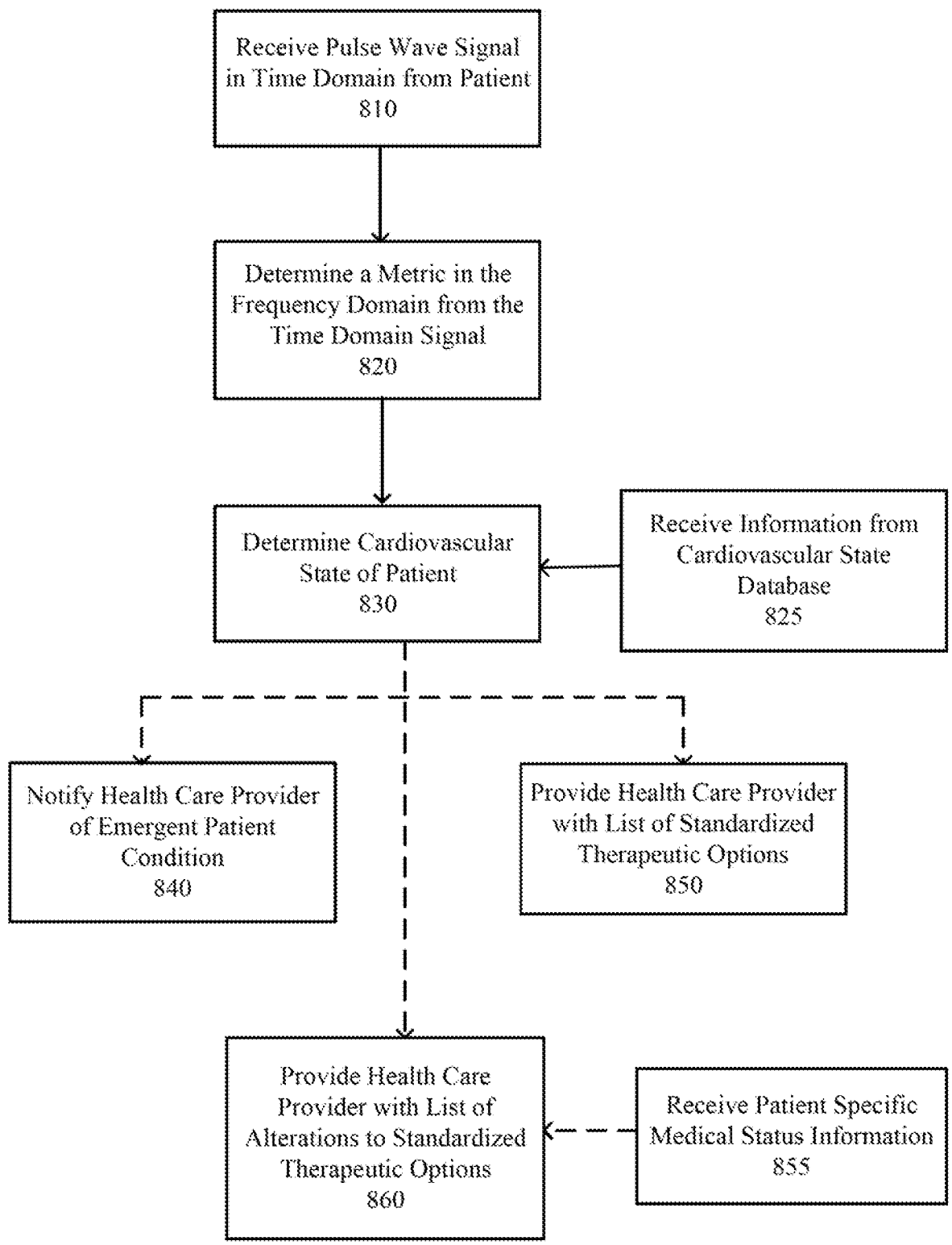
FIG. 8 is a flow chart of an illustrative method of determining a cardiovascular state of a patient in accordance with some embodiments.

FIG. 8 is a flow chart summarizing an illustrative method of determining at least a cardiovascular state of a patient using a physiological monitoring device. The monitoring device may receive 810 one or more time domain signals from a patient including, for example, a pulse wave signal. The monitoring device may determine 820 at least one metric in the frequency domain from the time domain signal. The monitoring device may receive 825 information from a cardiovascular state database and, in conjunction with the one or more frequency domain metrics, may determine 830 a cardiovascular state of the patient.

In addition to the method disclosed above, the monitoring device may include optional capabilities. For example, the monitoring device may notify 840 a health care provider or other user of possible emergent patient conditions upon determining 830 the cardiovascular state of the patient. In another example, the monitoring device may provide 850 a health care provider with one or more lists of standardized therapeutic procedure options. The list may be generated by the device from data received from an additional therapeutic database. The list of therapeutic options may also be ranked according to a metric of effectiveness. The monitoring device may also provide 860 a health care provider or user with a list of alterations or modifications to one or more standardized therapeutic options based on the patient status as determined at the time of patient monitoring. Patient status at the time of monitoring may include, without limitation, blood pressure measurements taken at the time of monitoring, changes in patient medication (for example, the patient forgot to take required medication prior to the monitoring session), and patient respiration at the time of monitoring. Such a list of alterations to standard therapies may be produced by the monitoring device in response to receiving 855 patient specific medical status information in addition to the metrics derived from the one or more sensing signals received 810 from the patient.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated in this disclosure, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can, of course, vary. It is also to be understood that the terminology used in this disclosure is for the purpose of describing particular embodiments only, and is not intended to be limiting.

With respect to the use of substantially any plural and/or singular terms in this disclosure, those having skill in the art can translate from the plural to the singular and/or from the singular to the plural as is appropriate to the context and/or application. The various singular/plural permutations may be expressly set forth in this disclosure for sake of clarity.

It will be understood by those within the art that, in general, terms used in this disclosure, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed in this disclosure also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed in this disclosure can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

From the foregoing, it will be appreciated that various embodiments of the present disclosure have been described for purposes of illustration, and that various modifications may be made without departing from the scope and spirit of the present disclosure. Accordingly, the various embodiments disclosed are not intended to be limiting, with the true scope and spirit being indicated by the following claims.

What is claimed is:

1. A method for determining a cardiovascular state of a patient in a stress condition, the method comprising:
   receiving, by a computing device, at least one signal in the time domain from at least one sensor in operative communication with the patient, the at least one signal being a pulse wave measurement from the patient;
   determining, with the computing device, at least one metric in the time domain from the at least one signal in the time domain;
   determining, with the computing device, at least one metric in the frequency domain from the at least one signal in the time domain;
   deriving, with the computing device, one or more sets of parameters using the at least one metric in the time domain and the at least one metric in the frequency domain, a set of parameters being associated with a particular cardiovascular state of a human;
   evaluating, with the computing device, temporal variations of the parameters within the one or more sets of parameters;
   determining, with the computing device, the cardiovascular state of the patient from a combination of the temporal variations of the parameters in the one or more sets of parameters and information from at least one database of cardiovascular states that are associated with the one or more sets of parameters.

2. The method of claim 1, wherein receiving, by a computing device, at least one signal in the time domain from at least one sensor comprises receiving the at least one signal in the time domain from at least one of a photo-optic sensor, a pressure transducer, a tonometry device, a strain gauge, an ultrasound device, an electrical impedance measurement device, and a radar device.

3. The method of claim 1, wherein receiving at least one signal in the time domain comprises receiving the at least one signal in the time domain from one or more of at least one sensor in physical contact with a surface of the patient and at least one sensor disposed within a natural cavity of the patient.

4. The method of claim 1, wherein receiving at least one signal in the time domain comprises receiving the at least one signal in the time domain from at least one sensor lacking a physical contact with the patient.

5. The method of claim 1, wherein receiving at least one signal in the time domain comprises receiving the at least one signal in the time domain the patient during one or more of an injury, a pathological process, a surgical procedure, a diagnostic procedure, a therapeutic procedure, and a result of a genetic pre-disposition.

6. The method of claim 1, wherein receiving at least one signal in the time domain comprises receiving the at least one signal in the time domain from the patient experiencing one or more of a cardiac myopathy, a chronic obstructive pulmonary disease, a chronic venous insufficiency, and a renal failure.

7. The method of claim 1, wherein receiving, by a computing device, at least one signal in the time domain comprises receiving, by the computing device, the at least one signal in the time domain from the at least one sensor in operative communication with the patient experiencing a surgical procedure requiring anesthesia.

8. The method of claim 1, wherein receiving at least one signal in the time domain comprises receiving the at least one signal in the time domain from the at least one sensor in operative communication with the patient experiencing one or more of a cardiovascular surgery, a pulmonary surgery, a renal surgery, an abdominal surgery, a neurovascular surgery, a procedure to treat one or more components of the cardiovascular system, a dialysis procedure, a cardiovascular rehabilitation procedure, a skeletal muscle rehabilitation procedure, an aquapheresis procedure, a cardiovascular reflex test, a cardiac function assessment procedure, a vascular non-compliance assessment procedure, or a tissue edema assessment procedure.

9. The method of claim 1, wherein determining, by the computing device, at least one metric in the frequency domain comprises determining, by the computing device, one or more of a fundamental frequency of the at least one signal, a frequency of one or more integer harmonics of the at least one signal, a phase value of the fundamental frequency, a phase value at the frequency of the one or more integer harmonics of the at least one signal, a frequency change in the fundamental frequency, a frequency change in one or more frequencies of the one or more integer harmonics, a phase change in the fundamental frequency, a phase change in one or more frequencies of the one or more integer harmonics, a power amplitude at the fundamental frequency of the at least one signal, a power amplitude at each frequency of the one or more integer harmonics of the at least one signal, a frequency dispersion about the fundamental frequency of the at least one signal, and a frequency dispersion about the frequency of the one or more integer harmonics of the at least one signal.

10. The method of claim 1, wherein determining, by the computing device, at least one metric in the frequency domain comprises:
    transforming, by the computing device, the at least one signal in the time domain into at least one signal in the frequency domain;
    selecting, by the computing device, at least one frequency domain feature of the at least one signal in the frequency domain; and
    normalizing, by the computing device, the at least one frequency domain feature to at least one frequency domain feature baseline.

11. The method of claim 10, wherein the at least one frequency domain feature comprises one or more of a fundamental frequency, a frequency of one or more integer harmonics of the fundamental frequency, a phase value of the fundamental frequency, a phase value at the frequency of the one or more integer harmonics of the at least one signal, a frequency change in the fundamental frequency, a frequency change in one or more frequencies of the one or more integer harmonics, a phase change in the fundamental frequency, a phase change in one or more frequencies of the one or more integer harmonics, a power at the fundamental frequency, a power at the frequency of the one or more integer harmonics of the fundamental frequency, a frequency of one or more sidebands of the fundamental frequency, a power at the frequency of the one or more sidebands of the fundamental frequency, a dispersion of frequencies about the fundamental frequency, a dispersion of frequencies about the one or more integer harmonics of the fundamental frequency, and a dispersion of frequencies within one or more sidebands of the fundamental frequency.

12. The method of claim 10, wherein the at least one frequency domain feature baseline comprises one or more of an average value of the frequency domain feature of the patient over time, a maximum value of the frequency domain feature of the patient over time, an average value of the frequency domain feature from a plurality of patients, a maximum value of the frequency domain feature from the plurality of patients, an average value of the frequency domain feature of the patient not in a stress condition, and a maximum value of the frequency domain feature of the patient not in a stress condition.

13. The method of claim 10, wherein normalizing, by the computing device, the at least one frequency domain feature to at least one frequency domain feature baseline comprises dividing, by the computing device, an at least one frequency domain feature value by an at least one frequency domain feature baseline value.

14. The method of claim 10, wherein normalizing, by the computing device, the at least one frequency domain feature to at least one frequency domain feature baseline comprises:
subtracting, by the computing device, an at least one frequency domain feature baseline value from an at least one frequency domain feature value to yield a numerator; and
dividing, by the computing device, the numerator by the at least one frequency domain feature baseline value.

15. The method of claim 1, wherein the information of the at least one database is contained in a memory storage device associated with the computing device.

16. The method of claim 1, wherein the information of the at least one database is contained in a memory storage device accessible to the computing device over a data communication link.

17. The method of claim 16, wherein the data communication link comprises one or more of an internet connection, a wireless connection, a telephonic connection, a LAN connection, a WAN connection, and a personal area network.

18. The method of claim 1, wherein the information in the database of cardiovascular states is obtained from a plurality of patients.

19. The method of claim 18, wherein the information in the database of cardiovascular states comprises one or more cardiovascular states for each of the plurality of patients.

20. The method of claim 18, wherein the information in the database of cardiovascular states comprises one or more metrics in the frequency domain from at least one signal in the time domain of a pulse wave measurement from each of the plurality of patients.

21. The method of claim 18, wherein the information in the database of cardiovascular states comprises one or more indicators of a medical status of each of the plurality of patients.

22. The method of claim 1, wherein the information in the database of cardiovascular states comprises a set of cardiovascular states and at least one set of parameters from the one or more metrics for each member of the set of cardiovascular states.

23. The method of claim 22, wherein the set of cardiovascular states comprises one or more of an obstructive sleep disorder state, an anesthesia induced hypovolemia state, a hemodialysis induced hypovolemia state, and a hemodialysis induced hypovolemia state of a patient having cardiac failure.

24. The method of claim 22, wherein the at least one set of parameters comprises a least one set of ranges of the one or more metrics.

25. The method of claim 22, wherein the at least one set of parameters comprises at least one set of temporal variations of the one or more metrics.

26. The method of claim 22, wherein the at least one set of parameters comprises at least one set of averages of the one or more metrics.

27. The method of claim 22, wherein the at least one set of parameters comprises at least one set of threshold values of the one or more metrics.

28. The method of claim 1, wherein the at least one metric in the time domain comprises one or more of a signal peak amplitude value of the at least one signal in the time domain, an average of a plurality of signal peak amplitude values of the at least one signal in the time domain, a time difference between an occurrence time of a first signal peak and a second signal peak of the at least one signal in the time domain, a dispersion of a plurality of signal peak amplitude values of the at least one signal in the time domain, and a dispersion of a plurality of time differences between an occurrence time of a first signal peak and a second signal peak of the at least one signal in the time domain.

29. The method of claim 1, further comprising providing, by the computing device, a notification to a health care provider of an emergent condition of the patient from the determined cardiovascular state.

30. The method of claim 29, wherein providing, by the computing device, a notification comprises providing one or more of an audible signal, a visual signal on a display, and a text message to a mobile communication device.

31. The method of claim 1, further comprising providing, by the computing device, a list of one or more therapeutic actions for the patient to a health care provider based on the determined cardiovascular state.

32. The method of claim 31, further comprising providing, by the computing device, a list of one or more therapeutic actions for the patient to a health care provider from at least one database of therapeutic protocols.

33. The method of claim 31, wherein the one or more therapeutic actions comprise one or more standard therapeutic protocols, or alterations to one or more standard therapeutic protocols.

34. The method of claim 31, further comprising:
receiving, by the computing device, at least one indicator of a medical status of the patient; and
providing, by the computing device, a list of one or more alterations to one or more standard therapeutic protocols to the health care provider for the patient from the at least one indicator of the medical status of the patient.

35. The method of claim 34, wherein receiving, by the computing device, at least one indicator of a medical status of the patient comprises receiving, by the computing device one or more of an indicator of a patient age, an indicator of a patient body mass, an indicator of a patient gender, an indicator of one or more patient co-morbidities, an indicator of one or more patient medications, an indicator of a dosage of each of the one or more patient medications, an indicator of one or more patient therapies, an indicator of one or more patient surgeries, and an indicator of one or more patient genetic predispositions to one or more pathologies.

36. The method of claim 1, further comprising updating, by the computing device, the at least one database of cardiovascular states with one or more of the at least one signal in the time domain, the at least one metric in the time domain, the at least one metric in the frequency domain, at least one set of parameters, and at least one indicator of a medical status of the patient.

37. The method of claim 36, further comprising determining, with the computing device, the cardiovascular state of the patient from the least one updated database of cardiovascular states.

* * * * *